United States Patent [19]

Beylin et al.

[11] Patent Number: 4,672,129

[45] Date of Patent: Jun. 9, 1987

[54] PROCESS FOR PREPARING SUBSTITUTED ANTHRA[1,9-CD]PYRAZOL-6(2H)-ONES

[75] Inventors: Vladimir G. Beylin; Om P. Goel; H.D. Hollis Showalter, all of Ann Arbor, Mich.

[73] Assignee: Warner-Lambert Company, Morris Plains, N.J.

[21] Appl. No.: 859,673

[22] Filed: May 5, 1986

[51] Int. Cl.$^4$ .......................................... C07D 231/54
[52] U.S. Cl. ..................................................... 548/357
[58] Field of Search ........................................ 548/357

[56] References Cited

U.S. PATENT DOCUMENTS 4,556,654 12/1985 Showalter et al. ................. 514/222

Primary Examiner—Henry R. Jiles
Assistant Examiner—Kurt G. Briscoe
Attorney, Agent, or Firm—Elizabeth M. Anderson

[57] ABSTRACT

An improved process for producing anthra[1,9-cd]-pyrazol-6(2H)-ones from 1,4-dichloro-5,8-disubstituted 9,10-anthracenediones. The process produces higher yields by using a new combination of protecting groups on the compounds which allows for easier and cleaner chromatographic resolution. The compounds produced have antibacterial, antifungal, antileukemic, and antitumor activity.

13 Claims, No Drawings

PROCESS FOR PREPARING SUBSTITUTED ANTHRA[1,9-CD]PYRAZOL-6(2H)-ONES

BACKGROUND OF THE INVENTION

The compounds of the present invention have been described in U.S. Pat. No. 4,556,654 herein incorporated by reference. A process for preparing the compounds is also described therein. That process includes a chromatographic separation and recrystallization procedures which are quite time consuming. P Another process for making anthra[1,9-cd]pyrazol-6(2H)-ones is described in U.S. Pat. No. 4,608,439. That process proceeds as follows:

Compounds of structural formula

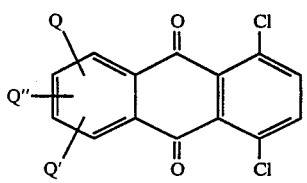

VI are reacted with a hydrazine of formula

H$_2$NNHDNHR' wherein Q, Q', and Q" may be the same or different and are H, benzyloxy, p-chlorobenzyloxy, and p-methoxybenzyloxy; D is straight or branched alkylene group of from two to eight carbon atoms; and R' is an alkyl group of from two to eight carbon atoms which may be substituted with OH, to produce a compound of structural formula

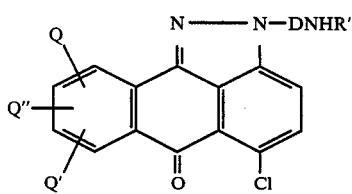

VII

Compounds of structural Formula VII are reacted with a benzyl halide in a suitable solvent to give compounds of structural formula

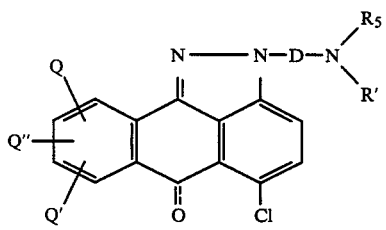

VIII wherein R$_5$ is benzyl.

Compounds of VIII are reacted with a diamine of the formula

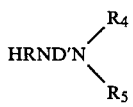

HRND'N$\diagdown_{R_5}^{R_4}$ wherein R$_4$ is H or an alkyl group of from one to eight carbon atoms and R$_5$ is as defined above, D' is a straight or branched alkylene group of from two to eight carbon atoms, to produce compounds of structural formula

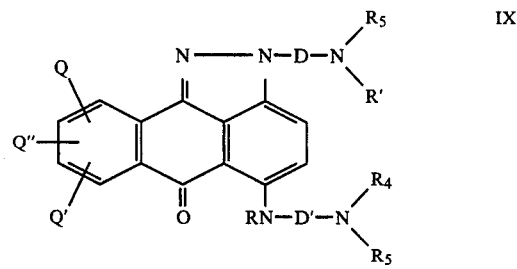

IX which are debenzylated by a standard procedure to produce compounds of the structural Formula V

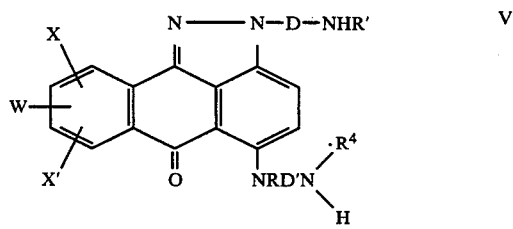

V wherein X, X', and W may be the same or different and are H or OH; R is H or alkyl of from one to six carbon atoms; D, D', R$_4$ and R' are as defined above.

The compounds are useful as antibacterial and antifungal agents.

Certain of the compounds show in vivo antileukemic activity. Certain of the compounds display in vitro activity against solid tumors.

SUMMARY

The present invention relates to an improved process for the preparation of substituted anthra[1,9-cd]pyrazol-6(2H)-ones. The present invention produces yields greater than those of previous processes by 6–15%. Also the present invention uses an easier and better chromatographic resolution method which is suitable for large scale production. The present process also involves a 1-step deprotection method which is suitable for commercial scale up.

The synthesis is for compounds having the structural formula

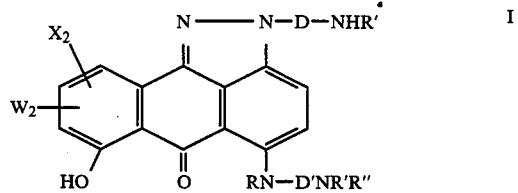

I wherein X$_2$ and W$_2$ may be the same or different and are H or OH or an alkoxy of from one to four carbon atoms; R is H or alkyl of from one to six carbon atoms; D and D' may be the same or different and are a straight or branched alkylene group of from two to eight carbon atoms, R' and R" are H or an alkyl group of from two to eight carbon atoms which may be substituted with OH.

The process proceeds as follows:

Compounds of structural formula

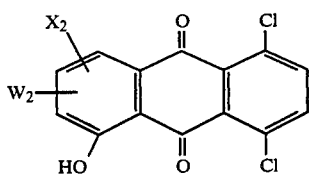
II wherein $X_2$ and $W_2$ are as defined above, are reacted with a substituted benzyl halide to give a compound of formula

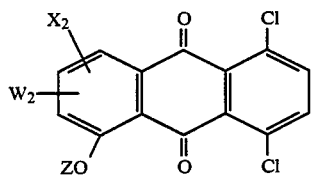
III wherein Z is a substituted benzyl wherein the substituents are described hereinafter.

Reacting a compound of formula III above with a hydrazine of formula $H_2NNHDNHR'$ wherein D and R' are as defined above gives isomers of the formulae

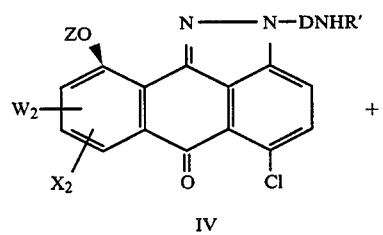
IV

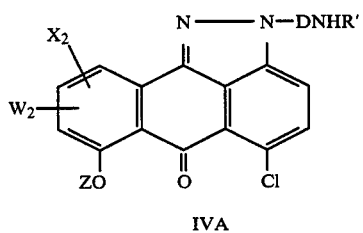
IVA

Treating the isomers with a dialkyldicarbonate or an alkylhaloformate or a benzylhaloformate produces compounds of formulae

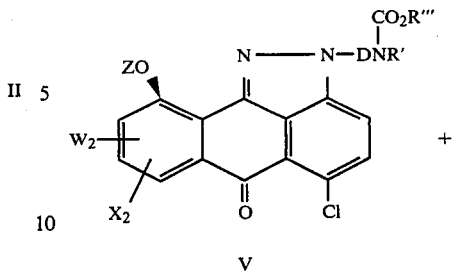
V

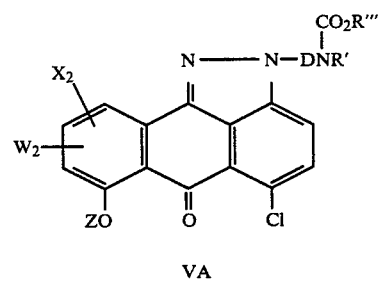
VA wherein R''' is an alkyl from one to eight carbon atoms, benzyl, or substituted benzyl, and D, R', $X_2$, $W_2$, and Z are as defined above or herein after.

These two isomers are then separated by column chromatography into V, the faster eluting component, and VA, the slower eluting component.

The isomer VA is treated with a strong acid to produce a compound of formula

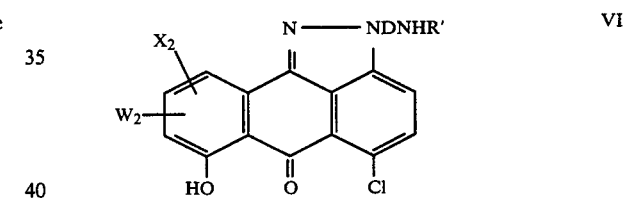
VI wherein X, W, D and R' are as defined above.

Compounds of this formula are then treated with a diamine of the formula

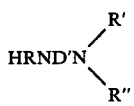

in which R, R', R'' and D' are defined above to produce the desired compound of formula I above.

DETAILED DESCRIPTION

For purposes of illustration the following schematic diagram shows alternative preparative procedures. Steps A, B, C, D, and E illustrate the process in U.S. Pat. No. 4,556,654. Steps A, B, F, G, and H illustrate a process described U.S. Pat. No. 4,608,439.

Steps I, J, K, L, and M are illustrative of the process of the present invention.

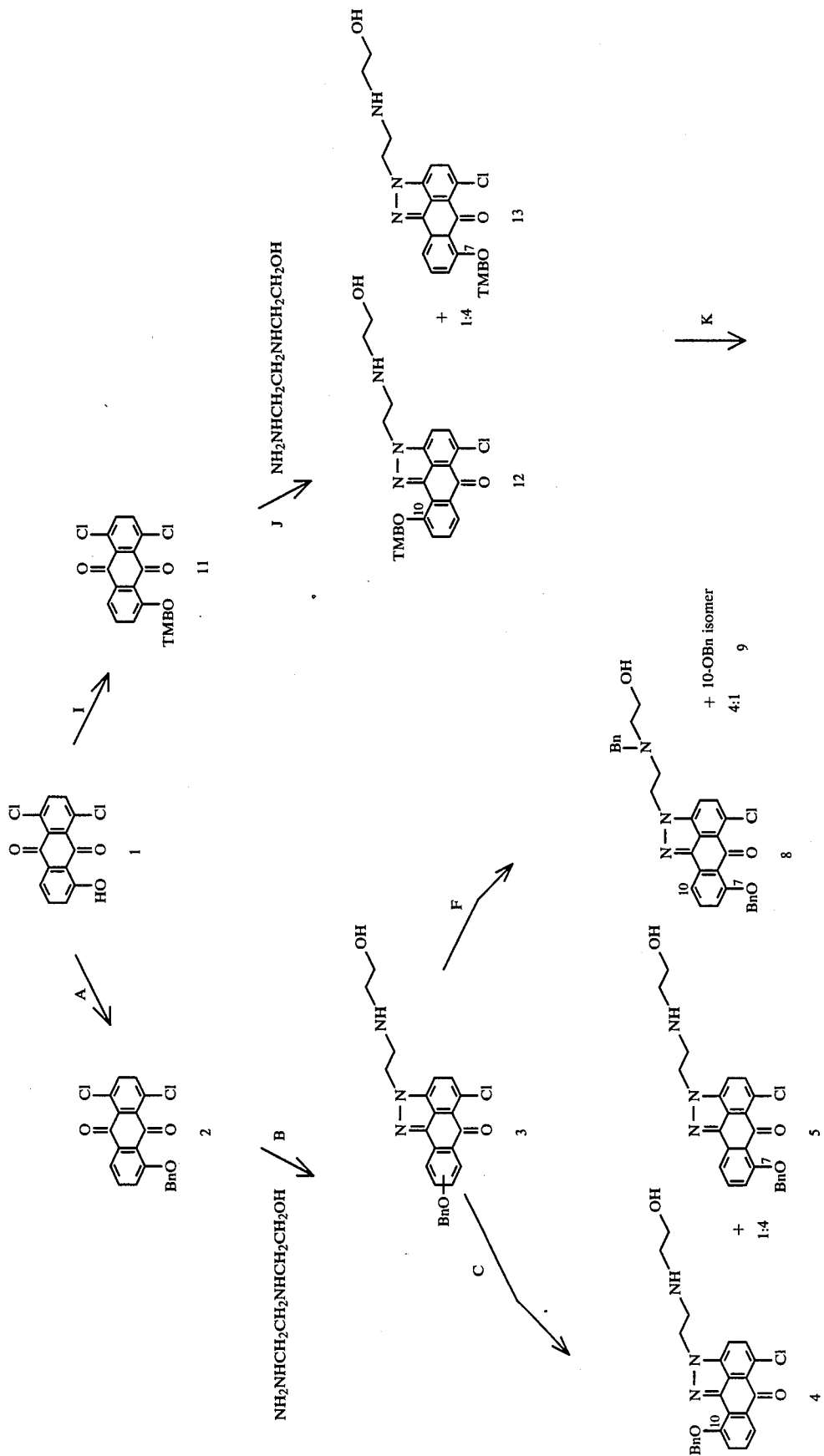

-continued
SCHEME I
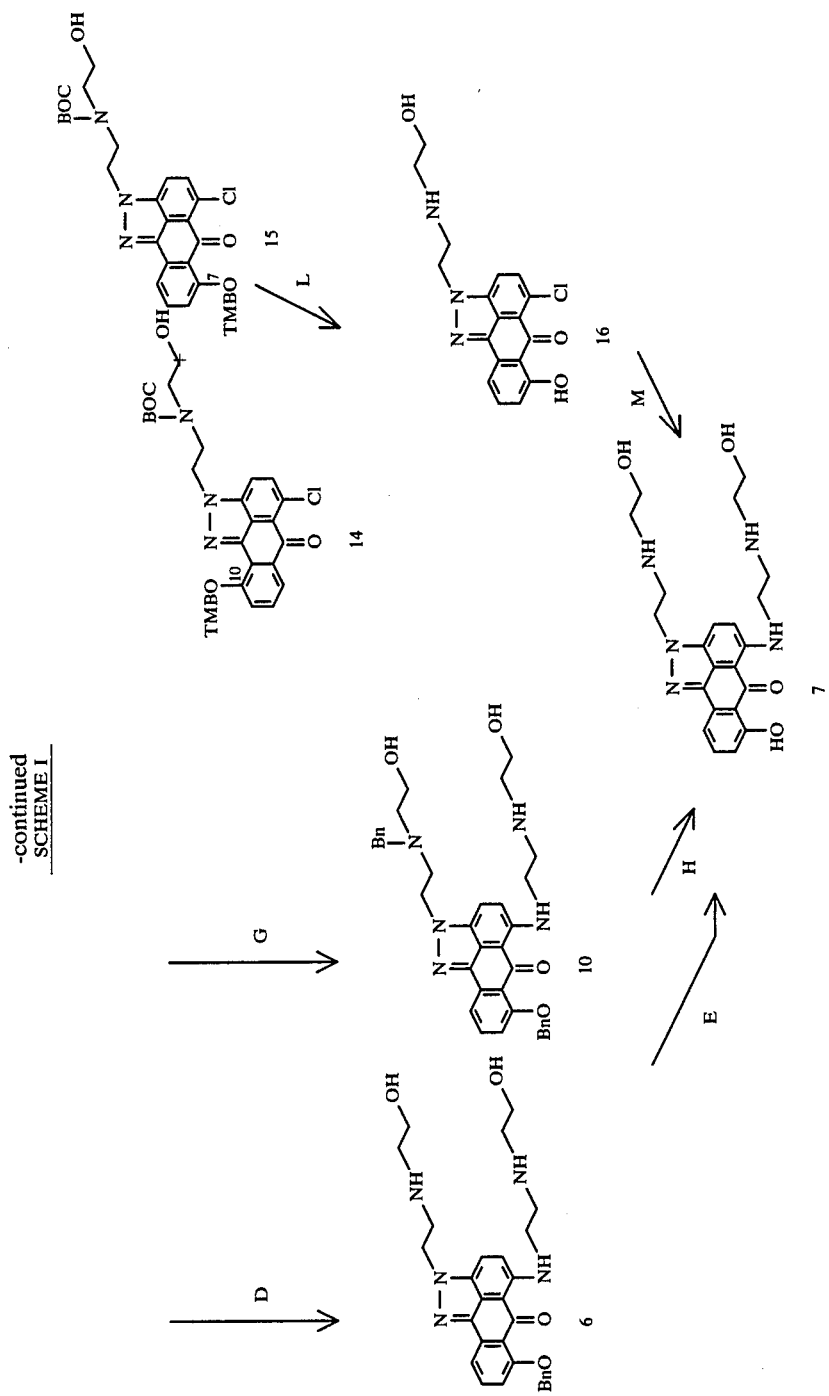
Bn = Benzyl
TMB = —CH₂— (2,4,6-trimethylphenyl)
BOC = —CO-t-butyl Schematic step I involves the reaction of compound II

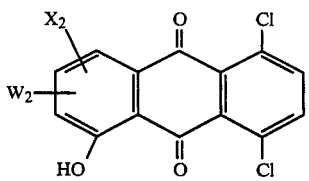

wherin X and W are defined above, with a substituted benzyl halide to form a protection group on the compound II. The benzyl halide optionally has one, two or three substituents. The substituents may be alkyl of from one to four carbon atoms, lower alkoxy of from one to four carbon atoms or halogen. The halide may be chloride or bromide; preferably it is chloride. Preferably the substituted benzyl halide is 2,4,6-trimethylbenzyl chloride.

The reaction is accomplished in any of a variety of reaction-inert solvents by mixing approximately equimolar amounts of compound II, an anhydrous carbonate, and a substituted benzyl halide in the chosen solvent at elevated temperature for 15–30 hours. The preferred carbonate is cesium carbonate. Use of a slight molar excess of the substituted benzyl halide may improve a particular yield.

Examples of suitable solvents are acetonitrile, acetone, dimethylsulfoxide, and N,N-dimethylformamide; particularly preferred are acetone-N,N-dimethylformamide combinations.

Most preferred form of step I is the reaction of compound II wherein $X_2$ and $W_2$ are H with 2,4,6-trimethylbenzyl chloride at reflux in approximately 3:1 by volume of acetone-N,N-dimethylformamide for 20–25 hours.

Schematic step J involves the reaction of compound III with a hydrazine of the formula $H_2NNHDNHR'$ wherein D and R' are as defined above. The reaction may be accomplished in a variety of inert solvents at elevated temperatures by mixing compound III with a hydrazine in a 1:3 molar ratio; such inert solvents include pyridine, dimethylsulfoxide, N,N-dimethylformamide, and acetonitrile. The reaction proceeds for 15 to 30 hours.

Preferred reaction conditions use acetonitrile as the solvent at reflux for 20–24 hours.

The hydrazine is a (hydroxyalkyl)aminoalkylhydrazine. Preferably the hydrazine is 2-[(2-hydrazinoethyl)amino]ethanol. The reaction produces isomers such as compounds IV and IVA in an approximate ratio of 1:4 when, for example, $X_2$ and $W_2$ are hydrogen.

In schematic step K a suspension containing the two isomers, compounds V and VA, in an inert solvent, such as dichloromethane, is treated with a dialkyldicarbonate or alkylhaloformate or a benzylhaloformate at room temperature for 1–4 hours. This produces lipophobic blocking groups on the two isomers in the positions shown in compounds V and VA in the scheme above as BOC.

The preferred carbonate is di-tert-butyl dicarbonate.
The preferred formate is benzylchloroformate.
The solution is evaporated to remove the solvent. The residue is dissolved in a suitable organic solvent system that separates the isomers by $\geq 0.15$ $R_f$ by thin layer chromatography. The solution is chromatographed to separate the two isomers. A preferred chromatographic separation uses a silica gel column and gradient elution with ethyl acetate:hexane in an initial ratio of approximately 1:1 and gradually increasing to a pure ethyl acetate.

This separation is practical on a large scale. Whereas, in contrast in step F of the scheme, separation of isomers by flash silica gel chromatography is practical only on a small scale as large quantities of silica gel are required.

In step C of the scheme the isomers can be only partially separated by flash silica gel chromatography.

In schematic step L both blocking groups (shown in scheme as BOC and TMB) are removed in one step by addition of a strong acid at room temperature. The preferred acid is HCl. The reaction can be carried out in a number of inert solvents; the preferred solvent is 1:4 dichloromethane:methanol.

In step M compound VI is reacted with a diamine of the formula

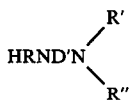

wherein R, D', R' and R" are described above. The reaction proceeds in a variety of inert solvents; pyridine is the preferred solvent. The reaction proceeds at an elevated temperature for 15–40 hours. Preferably the temperature is between 70°–115° C. The most preferred temperature is between 80°–90° C. The reaction time is preferably 19–23 hours. Compounds of structural formula I are produced.

Examples 1–4 illustrate the process described in U.S. Pat. No. 4,556,654.

Examples 5–7 describe the process of U.S. Pat. No. 4,608,439.

Examples 8–12 are meant to be illustrative of the present invention. These examples are presented to exemplify the invention and are not to be construed as limiting the invention's scope.

EXAMPLE 1

1,4-Dichloro-5-(phenylmethoxy)-9,10-anthracenedione (2)

A mechanically stirred mixture of 177.2 g (0.605 mol) of 1,4-dichloro-5-hydroxy-9,10-anthracenedione (1, British Pat. No. 1,029,448), 83.5 g (0.605 mol) of powdered anhydrous potassium carbonate, 79 ml (0.675 mol) of benzyl bromide, and 1.7 l of dry acetone was heated at reflux for three days. The initial dark brown suspension changed to an olive green color signaling the end of the reaction. The mixture was filtered hot and the salts were washed with hot acetone. The cooled filtrate was concentrated to ~½ of its volume. The yellow precipitate was collected by filtration, washed with acetone and methanol, and dried at 200 mm/50° C./12 hr to leave 201.2 g (87%) of 2, mp 122°–126° C.

The combined filtrates were evaporated to dryness. The residual solid was crystallized from hot acetone to afford 14.6 g (6%) of additional 2, mp 122°–126° C. Total yield=93%.

EXAMPLE 2

5-Chloro-2-[2-[(2-hydroxyethyl)amino]ethyl-7-(phenylmethoxy)anthra[1,9-cd]pyrazol-6(2H)-one (5)

A mixture of 38.3 g (0.1 mol) of 1,4-dichloro-5-(phenylmethoxy)-9,10-anthracenedione (2), 33 g (0.277 mol) of 2-[(2-hydrazinoethyl)amino]ethanol and 200 ml of pyridine was stirred at 80° C. for 16 hr. The mixture was concentrated in vacuo to an oil which was distributed between dichloromethane and water. The organic layer was washed with water, dried, and concentrated to 40.7 g of a residue showing a ~1:4 ratio of 4:5 which was purified by chromatography on 1 kg of silica gel (230–400 mesh) eluting with dichloromethane:methanol (9:1). Concentration of fractions containing the faster eluting component gave 6 g of a solid that was triturated from ethanol to leave 2.5 g of isomer 4, mp 172°–175° C., 94% pure by HPLC with 1% of isomer 5. Concentration of fractions containing the slower eluting component gave 6 g of a solid that was crystallized from ethanol to leave 4.6 g of isomer 5, mp 142°–143° C., 98% pure by HPLC with 2% of 4. Yield of crude 5 after column chromatography=35%. Yield of pure 5 following crystallization=10%.

Repetition of the above reaction was carried out on a mixture of 50.0 g (0.130 mol) of 1,4-dichloro-5-(phenylmethoxy)-9,10-anthracenedione, 46.5 g (0.390 mol) of 2-[(2-hydrazinoethyl)amino]ethanol and 300 ml of dimethylsulfoxide at 25° C. for 2.75 days. The mixture was poured into 2.5 l of ice water. The gummy residue was collected by filtration then dissolved in dichloromethane. The solution was washed with water, dried, and concentrated to leave 50.1 g of a gummy residue. The residue was dissolved in 750 ml of dichloromethane:methanol (4:1) and filtered through 500 g of silica gel (70–230 mesh) eluting with dichloromethane:methanol (4:1) until all of the isomeric mixture 3 had been collected. Concentration of the product fractions gave 35 g of a gum which was triturated with methanol to give 25 g of a yellow solid 3 containing 4 and 5 in a ~1:4 ratio by HPLC (crude yield of 5=34%). Partial separation of isomers by column chromatography was carried out as described above.

EXAMPLE 3

2-[2-[(2-Hydroxyethyl)amino]ethyl]-5-[[2-[(2-hydroxyethyl)amino]ethyl]amio]-7-(phenylmethoxy)anthra[1,9-cd]pyrazol-6(2H)-one (6)

A mixture of 2.2 g (4.9 mmol) of 5-chloro-2-[(2-hydroxyethyl)amino]ethyl-7-(phenylmethoxy)anthra[1,9-cd]-pyrazol-6(2H)-one (5), 4.5 ml (44.5 mmol) of 2-(2-aminoethylamino)ethanol, 0.5 g of anhydrous potassium bicarbonate, and 15 ml of pyridine was stirred at reflux for 24 hr. The mixture was filtered and concentrated in vacuo to leave an oil which was layered with 2-propanol. A precipitate formed at 25° over a three day period. The solids were collected by filtration, then crystallized from 2-propanol to give, after drying, 1.0 g of pure 6, mp 157°–159° C. Purification of filtrates was carried out by chromatography on 115 g of silica gel (230–400 mesh) utilizing gradient elution with 5, 10, and 15% methanol in dichloromethane:triethylamine (99:1). Concentration of product fractions gave a solid which was triturated from 2-propanol to give 0.3 g of additional 6, mp 157°–159° C. Total yield of 6=50%.

Repetition of the above reaction was carried out on a mixture of 10.0 g (22.2 mmol) of 5 and 38.6 g (370 mmol) of 2-(2-aminoethylamino)ethanol at 160° for 24 hr. The cooled mixture was diluted with 200 ml of 2-propanol and allowed to stand at 5° overnight. The solids were collected by filtration to give 10.3 g of crude 6 which was purified by column chromatography on 145 g of silica gel (70–230 mesh) eluting with dichloromethane:methanol:triethylamine:acetic acid (2:1:0.2:0.1). Concentration of product fractions gave a solid which was triturated with ~1:1 2-propanol:diethyl ether to give 7.5 g of 6 complexed with 3.0 equivalents of acetic acid, mp 115°–119°. Yield of pure 6=48%.

EXAMPLE 4

7-Hydroxy-2-[2-[(2-hydroxyethyl)amino]ethyl]-5-[[2-[(2-hydroxyethyl)amino]ethyl]amino]anthra[1,9-cd]pyrazol-6(2H)-one, dihydrochloride (7)

A mixture of 3.1 g of (6.0 mmol) of 2-[2-[(2-hydroxyethyl)amino]ethyl]-5-[[2-[(2-hydroxyethyl)amino]ethyl]amino]-7-(phenylmethoxy)anthra[1,9-cd]pyrazol-6(2H)-one (6) in 150 ml of glacial acetic acid was hydrogenated over 1.0 g of 20% palladium hydroxide on carbon at atmospheric pressure and at room temperature until 170 ml of hydrogen had been absorbed. The mixture was filtered through celite and concentrated under vacuum. The residue was dissolved in boiling 2-propanol. The solution was treated with an excess of hydrogen chloride in 2-propanol and cooled. The red-orange precipitate was collected, washed with 2-propanol then diethyl ether, and dried at 80° C. under vacuum for 7 hr to give 3.0 g (97%) of 7, containing 0.6 equivalent of water, mp 257°–262° C. (dec) with prior scintering. Overall isiolated yield via steps A, B, C, D, and E=4.3%.

EXAMPLE 5

5-Chloro-2-[2-[(2-hydroxyethyl)(phenylmethyl)amino]ethyl]-7-(phenylmethoxy)anthra[1,9-cd]pyrazol-6(2H)-one (8)

A mixture of 14.5 g (32.3 mmol) of 5-chloro-2-[2-[(2-hydroxyethyl)]amino]-7-(phenylmethoxy)anthra[1,9-cd]pyrazol-6(2H)-one (5) and its 10-phenylmethoxy isomer (4), ~4:1 respectively by HPLC, 3.9 ml of α-bromotoluene, 6.5 g of potassium bicarbonate, and 140 ml of N,N-dimethylformamide was stirred at room temperature for 18 hr. The mixture was diluted with 500 ml of water and extracted with three 200 ml portions of dichloromethane. The combined organic extracts were washed with water, dried, and concentrated to an oil which was purified by chromatography on 600 g of silica gel (230–400 mesh). Elution with ethyl acetate:hexane (3:2) followed by concentration of product fractions gave the faster eluting component as a solid. Crystallization from acetonitrile afforded 3.55 g of pure isomer 9, mp 130°–134° C. Elution with ethyl acetate followed by concentration of product fractions afforded 9.2 g (66%) of slower eluting isomer 8 as a syrup which could not be crystallized.

EXAMPLE 6

5-[[2-[(2-Hydroxyethyl)amino]ethyl]amino]-2-[2-[(2-hydroxyethyl)(phenylmethyl)amino]ethyl]-7-(phenylmethoxy)anthra[1,9-cd]pyrazol-6(2H)-one (10)

A mixture of 6.0 g (11.2 mmol) of 5-chloro-2-[2-[(2-hydroxyethyl)(phenylmethyl)amino]ethyl]-7-(phenylmethoxy)anthra[1,9-cd]pyrazol-6(2H)-one (8) and 12.2 ml (121 mmol) of 2-(2-aminoethylamino)-ethanol was heated at 160° C. for 24 hr. The cooled mixture was diluted with 60 ml of 2-propanol then maintained at 0°–5° C. for several days. The precipitate was collected, washed with cold 2-propanol then diethyl ether, and dried at 60° C. under vacuum for 18 hours to give 4.1 g (60%) of 10, mp 134°–137° C., 97% pure by HPLC.

EXAMPLE 7

7-Hydroxy-2-[2-[(2-hydroxyethyl)amino]ethyl]-5-[[2-[(2-hydroxyethyl)amino]ethyl]amino]anthra[1,9-cd]pyrazol-6(2H)-one, dihydrochloride (7)

A mixture of 4.4 g (7.2 mmol) of 5-[[2-[(2-hydroxyethyl)amino]ethyl]amino]-2-[2-[(2-hydroxyethyl)(phenylmethyl)amino]ethyl]-7-(phenylmethoxy)anthra[1,9-cd]-pyrazol-6(2H)-one (10) in 60 ml of methanol and 20 ml of glacial acetic acid was hydrogenated over 250 mg of 20% palladium hydroxide on carbon at atmospheric pressure and at room temperature until 330 ml of hydrogen had been absorbed. The mixture was worked up as described in Example 4 to give 3.6 g (100%) of 7, containing 0.2 equivalent of water, mp 255°–260° C. (dec) with prior scintering. Overall isolated yield via steps A, B, F, G, and H=13%.

EXAMPLE 8

1,4-Dichloro-5-[(2,4,6-trimethylphenyl)methoxy]-9,10-anthracenedione (11)

A mechanically stirred mixture of 550.6 g (1.88 mol) of 1,4-dichloro-5-hydroxy-9,10-anthracenedione (1), 413.4 g (2.14 mol) of anhydrous cesium carbonate, 444 g, (2.4 mol) of 2,4,6-trimethylbenzyl chloride, 7.06 l of acetone, and 2.31 l of N,N-dimethylformamide was heated at reflux for 23 hr. During this period, additional portions of 2,4,6-trimethylbenzyl chloride (2.5 hr, 31.7 g; 6.5 hr, 63.4 g; 20 hr, 31.7 g) and one portion of cesium carbonate (20 hr, 4.8 g) were added. The mixture was cooled to 10° C. The precipitate was collected by filtration, washed successively with hot water and methanol, then dried at 7–9 mm/50° C./20 hr to leave 621 g (78%) of 11, mp 216°–218° C., 97.9% pure by HPLC.

EXAMPLE 9

5-Chloro-2-[2-[(2-hydroxyethyl)amino]ethyl]-7-[(2,4,6-trimethylphenyl)methoxy]anthra[1,9-cd]pyrazol-6(2H)-one (13)

A mechanically stirred mixture of 310 g (0.73 mol) of 1,4-dichloro-5-[(2,4,6-trimethylphenyl)methoxy]-9,10-anthracenedione, 260 g (2.19 mol) of 2-[(2-hydrazinoethyl)amino]ethanol, 381 ml (2.19 mol) of N,N-diisopropylethylamine, and 4.8 l of acetonitrile was heated at reflux for 22 hr. The cooled mixture was concentrated in vacuo to leave a residue, showing a ~1:4 ratio of 12:13, that was triturated with water. The solids were collected by filtration, washed with methanol, and dried at 220 mm/50° C./18 hr to leave 237 g (66%) of crude 13, mp 147°–158° C.

The crude product was dissolved in a mixture of 11.5 l of N,N-dimethylformamide and 10.7 l of methanol and the solution was stored at −17° C. overnight. The precipitated solids were collected by filtration, washed and dried as above to give 144 g (40% overall yield; 61% recrystallization yield) of pure 13, mp 179.5°–183.5° C., 98.1% isomeric purity by HPLC.

EXAMPLE 10

[5-Chloro-6-oxo-7-[(2,4,6-trimethylphenyl)methoxy]-anthra[1,9-cd]pyrazol-2(6H)-yl](2-hydroxyethyl)carbamic acid, 1,1-dimethylethyl ester (15)

A suspension containing 411.5 g (0.84 mol) of crude 5-chloro-2-[2-[(2-hydroxyethyl)amino]ethyl]-7-[(2,4,6-trimethylphenyl)methoxy]anthra[1,9-cd]pyrazol-6(2H)-one (13) and its C-10 isomer (12), ~4:1 respectively by HPLC, 247.3 g (1.1 mol) of di-tert-butyl dicarbonate, and 3.4 l of dichloromethane was stirred at room temperature for 2 hr. The dark solution was evaporated in vacuo to leave 825 g of a dark syrup which was dissolved in 1.5 l of ethyl acetate:hexane (1:1). The solution was chromatographed on 10 kg of silica gel (230–400 mesh) utilizing gradient elution with ethyl acetate:hexane (from 50:50 to 100:0). Concentration of fractions containing the faster moving component gave a residual solid whose trituration from methanol left 82.3 g (17%) of pure 14, mp 185°–187° C., as a yellow solid; TLC (SiO$_2$, ethyl acetate), R$_f$=0.42.

Concentration of fractions containing the slower eluting component left a residual solid which was crystallized from ethyl acetate to give 281.3 g (57%) of pure 15, mp 185°–187° C., as a yellow solid; TLC (SiO$_2$, ethyl acetate), R$_f$=0.26. HPLC shows 99.5% purity.

EXAMPLE 11

5-Chloro-2-[2-[(2-hydroxyethyl)amino]ethyl]-7-hydroxyanthra[1,9-cd]pyrazol-6(2H)-one (16)

To a stirred ice-cold solution containing 103.5 g (0.175 mol) of 5-chloro-6-oxo-7-[(2,4,6-trimethylphenyl)methoxy]anthra[1,9-cd]pyrazol-2-(6H)-yl](2-hydroxyethyl)carbamic acid, 1,1-dimethylethyl ester (15) and 1 l of dichloromethane:methanol (1:4) was bubbled anhydrous hydrogen chloride until the temperature reached 20° C. The bubbling was stopped and the mixture cooled to 6°–8° C. This process was repeated three times until a reddish precipitate began to form. The bubbling was stopped and the mixture was allowed to warm to room temperature. After overnight stirring the precipitate was collected by filtration, washed successively with dichloromethane then hexane, and dried at 220 mm/60° C./overnight to leave 61.6 g (89%) of pure 16, mp 264°–266° C. (dec), 98.3% pure by HPLC.

EXAMPLE 12

7-Hydroxy-2-[2-[(hydroxyethyl)amino]ethyl]-5-[[2-[(hydroxyethyl)amino]ethyl]amino]anthra[1,9-cd]pyrazol-6(2H)-one (7)

A solution of 3.94 g (10 mmol) of 5-chloro-2-[2-[(2-hydroxyethyl)amino]ethyl]-7-hydroxyanthra[1,9-cd]pyrazol-6(2H)-one (16), 10.5 ml (100 mmol) of 2-(2-aminoethylamino)ethanol, and 27 ml of pyridine was stirred under nitrogen at 82° C. for 21 hr. It was cooled to 23° C., diluted with 35 ml of 2-propanol, and the resultant suspension stirred at 5° C. for 2 hr. The precipitate was collected by filtration, washed successively with cold 2-propanol then hexane, and dried at 220 mm/60° C./overnight to leave 3.4 g (80%) of pure 7 as the free base, mp 149°–150.5° C. (dec), 98.5% pure by HPTLC.

A 3.2 g (7.5 mmol) sample of the free base was suspended in methanol and treated with an excess of hydrogen chloride in 2-propanol. The mixture was heated to reflux then maintained at 0° C. for 2 hr. The precipitate was collected by filtration, washed with methanol, dried at 220 mm/60° C./overnight, and allowed to equilibrate in air to afford 3.4 g (91%) of 7, mp 271°–273° C. (dec) which analyzes for 2HCl.0.8H$_2$O and is 99.5% pure by HPLC. Overall isolated yield via steps I, J, K, L, and M=19%.

Other embodiments of the invention will be apparent to one skilled in the art. The specification and the above examples are intended as exemplary only, the true scope and spirit of the invention being indicated by the following claims.

We claim:

1. A process for the preparation of a substituted anthra[1,9-cd]pyrazol-6(2H)-one having the formula

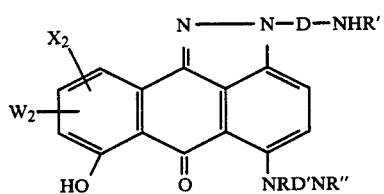

I wherein X$_2$ and W$_2$ may be the same or different and are H, OH, or an alkoxy of from one to four carbon atoms, R is H or alkyl of from one to six carbon atoms; D and D' may be the same or different and are a straight or branched alkylene group of from two to eight carbon atoms, R' and R" are H or an alkyl group of from two to eight carbon atoms which may be substituted with OH which comprises:

(a) reacting a compound of the formula

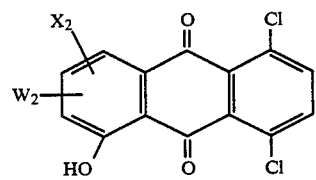

II wherein X$_2$ and W$_2$ are as defined above, with a substituted benzyl halide to give a compound of formula

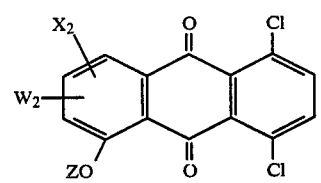

III wherein Z is a substituted benzyl, the substituents being an alkyl of from one to four carbon atoms, lower alkoxy of from one to four carbon atoms, or halogen;

(b) reacting a compound of structural Formula III with a hydrazine of formula H$_2$NNHDNHR', wherein D and R' are as defined above, to give isomers of formulae

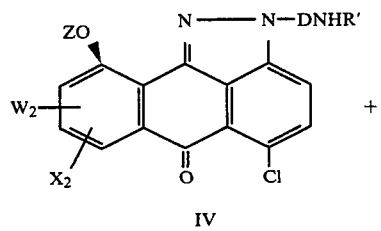

IV

+

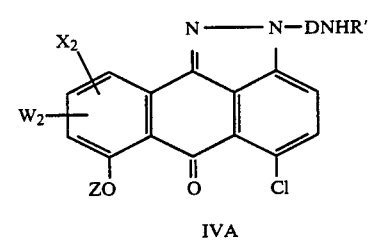

IVA wherein X$_2$, W$_2$, Z, D, and R' are as defined above;

(c) treating the above isomers with a dialkyl-dicarbonate, alkylhaloformate or a benzylhaloformate to produce compounds of formulae

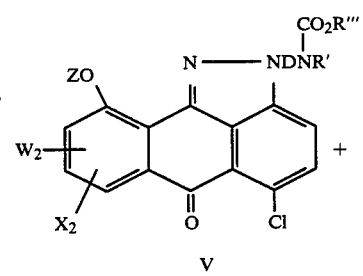

V

+

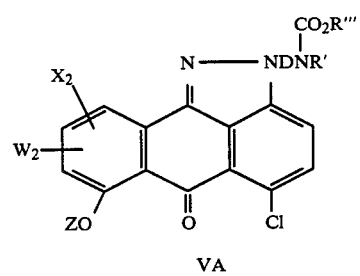

VA wherein R' R''' is an alkyl from one to eight carbon atoms, or benzyl, and X$_2$, W$_2$, Z, D, and R' are defined above;

(d) separating by column chromatography the two isomers V and VA, (e) treating isomeric VA with a strong acid to produce a compound of formula

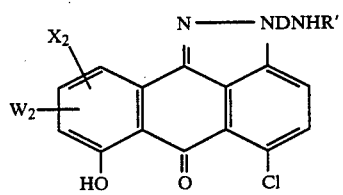

VI wherein X$_2$, W$_2$, D, and R' are as defined above;

(f) treating a compound of Formula VI with a diamine of the formula

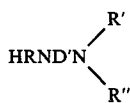

in which R, R', R", and D' are as defined above in an inert solvent, to produce a compound of structural Formula I above.

2. The process of claim 1, wherein in step (a) the substituted benzyl halide is a trialkylbenzyl halide and Z is the corresponding trialkylbenzyl group.

3. The process of claim 2, wherein in step (a) the trialkylbenzyl halide is 2,4,6-trimethylbenzyl chloride and Z is

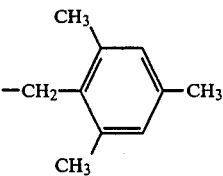

4. The process of claim 1, wherein in step (b) the hydrazine is a (hydroxyalkyl)aminoalkylhydrazine.

5. The process of claim 4, wherein in step (b) the hydrazine is 2-[(2-hydrazinoethyl)amio]-ethanol.

6. The process of claim 1, wherein in step (c) the reagent added is a dialkyldicarbonate.

7. The process of claim 1, wherein in step (c) the dialkyldicarbonate is di-tert-butyl dicarbonate.

8. The process of claim 1, wherein the step (e) the strong acid is hydrogen chloride.

9. The process of claim 1, wherein in step (f) the diamine is an (aminoalkyl)aminoalkanol.

10. The process of claim 1, wherein in step (f) the diamine is 2-(2-aminoethylamino)ethanol.

11. The process of claim 1, wherein in step (f) the inert solvent is pyridine.

12. The process of claim 1, wherein in step (f) the reaction proceeds from fifteen to forty hours at a temperature between 70° C. and 115° C.

13. The process of claim 1, wherein in step (f) the reaction proceeds for nineteen to twenty-three hours at a temperature between 80° and 90° C.

* * * * *

UNITED STATES PATENT AND TRADEMARK OFFICE
CERTIFICATE OF CORRECTION

PATENT NO. : 4,672,129
DATED : June 9, 1987
INVENTOR(S) : Vladimir G. Beylin, Om P. Goel, H. D. Hollis Showalter It is certified that error appears in the above—identified patent and that said Letters Patent is hereby corrected as shown below:

Column 15, line 20, Figure I: Insert R' before R".

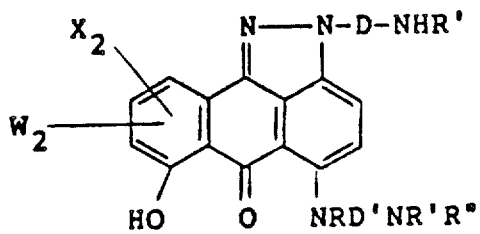

I

Signed and Sealed this

Twenty-second Day of September, 1987

Attest:

DONALD J. QUIGG

Attesting Officer     Commissioner of Patents and Trademarks